United States Patent
Morris et al.

(10) Patent No.: US 6,792,619 B1
(45) Date of Patent: Sep. 21, 2004

(54) EYEGLASSES AND PENCIL RETAINING ASSEMBLY

(76) Inventors: David Todd Morris, 125 Bridgestone Cove, Fayetteville, GA (US) 30215; Phillip Everett Brooks, 500 Westpark Dr. Suite 400, Peachtree City, GA (US) 30269

( * ) Notice: Subject to any disclaimer, the term of this patent is extended or adjusted under 35 U.S.C. 154(b) by 0 days.

(21) Appl. No.: 10/396,995

(22) Filed: Mar. 25, 2003

(51) Int. Cl.[7] .................................................. A61F 9/00
(52) U.S. Cl. ......................... 2/10; 2/209.13; 224/181; 351/155
(58) Field of Search ............................. 2/209.13, 175.1, 2/195.1; 351/155, 158; 224/181

(56) References Cited

U.S. PATENT DOCUMENTS

| | | | |
|---|---|---|---|
| 4,179,753 A | * 12/1979 | Aronberg et al. | ................. 2/10 |
| 4,852,221 A | * 8/1989 | Antonucci | ................. 24/10 R |
| 5,066,154 A | * 11/1991 | Renaud | ................. 401/131 |
| 5,082,225 A | 1/1992 | Nespoli | |
| 5,102,024 A | * 4/1992 | Boersma et al. | ............. 224/181 |
| 5,412,545 A | * 5/1995 | Rising | ......................... 362/105 |
| 5,454,120 A | 10/1995 | Rowlands | |
| 5,509,144 A | 4/1996 | Soergel | |
| 5,867,874 A | * 2/1999 | Simpson | ....................... 24/336 |
| 5,887,287 A | * 3/1999 | Potochnik | ................... 2/209.13 |
| 6,185,748 B1 | 2/2001 | DeChambeau | |
| 6,298,495 B1 | 10/2001 | Tontani | |
| 6,397,396 B1 | 6/2002 | Vibert | |
| 6,442,764 B1 | * 9/2002 | Badillo et al. | .............. 2/209.13 |
| 6,647,554 B1 | * 11/2003 | Yan | ............................ 2/209.13 |

* cited by examiner

*Primary Examiner*—Katherine Moran

(57) ABSTRACT

An implement holder to be attached to a cap, hat, clothing or other item is provided. The holder is a single unit, which can be integrated into the construction of the cap, hat, clothing or other item or removably attached to the outer surface of the article. The two sides of the unit are attached and form a loop for receiving a pencil, pen or other elongated implement. The unit additionally contains an adjustable flap for receiving the temple of eyewear, including glasses, sunglasses, or protective eye gear. The outer side of the unit is smooth and is designed to receive identifying or advertising indicia.

3 Claims, 2 Drawing Sheets

EYEGLASSES AND PENCIL RETAINING ASSEMBLY

CROSS-REFERENCE TO RELATED APPLICATIONS

Not Applicable

FEDERALLY SPONSORED RESEARCH

Not Applicable

SEQUENCE LISTING OR PROGRAM

Not Applicable

BACKGROUND OF THE INVENTION—FIELD OF INVENTION

The present invention relates to a retaining assembly for eyeglasses and other implements that can be an integral part of an item such as a hat or cap or can be removably attached to an item such as a hat, cap or clothing.

BACKGROUND OF THE INVENTION— DISCUSSION OF PRIOR ART

Glasses, particularly sunglasses, are a feature of modem life. Glasses may, at times, interfere with the wearer's eyesight. It is generally not convenient to remove the glasses and place them in a storage case. The wearer may not have access to a storage case.

Additionally, many outdoor activities, such as golf require a pencil or instrument for making marks or keeping score. People have placed this instrument behind their ear for storage when not in use. This is not a secure storage location and the instrument is often misplaced during the activity.

In any of the above cases, it is desirable to have an alternative means of securely carrying the glasses and instrument when they are not in use. This will prevent them from being damaged or lost.

The prior art provides a number of different approaches to the glasses problem. U.S. Pat. No. 5,082,225 issued to Nespoli Jan. 21, 1992, describes a clip, which allows sunglasses to be attached to the visor of the cap. This visor attachment does not allow storage for a pencil, and only allows the glasses to be placed in the front position. U.S. Pat. No. 6,298,495 issued to Tontani Oct. 9, 2001, describes an insertion hole in the edge of the cap that allows the temple of the glasses to be placed into. The hat must be removed from the wearer's head to allow glasses to be inserted into the holes. There is no storage for pencils. U.S. Pat. No. 5,867,874 issued to Simpson Feb. 9, 1999, describes a rigid plastic clip that can be attached to the cap for holding glasses and a pencil. This clip is a separate device and can easily be lost or fail off the cap or hat. Additionally, these inventions suffer in comparison to the current invention in that they require a separate clip or do not securely hold the glasses or pencil during strenuous activity.

BACKGROUND OF THE INVENTION— OBJECTS AND ADVANTAGES

Accordingly, several objects and advantages of the present Patent Application of David Morris and Phillip Brook for "Eyeglasses and pencil retaining assembly" are:
a) To provide a assembly for securely attaching glasses to a hat, cap, clothing or other item;
b) To provide a assembly for securely attaching a tool, such as a pencil, to a hat, cap, clothing or other item;
c) To allow the wearer, of a cap or hat the option of securing the glasses in the front or back of the cap or hat;
d) To provide an assembly that will be an attractive addition to the cap, hat, clothing or other item;
e) To allow the wearer to attach the glasses and a tool, such as a pencil, to the cap, hat, clothing or other item without requiring the wearer to remove the cap, hat, clothing or other item;
f) To allow additional surface area on the sides of the cap, hat or other item for the placement of identifying or advertising indicia similar to an advertising billboard.

The current invention, besides being inexpensive, has a number of advantages over the prior art. Most importantly from a functional standpoint, the holder is an integral part of or securely affixed to an article such as the wearer's hat and cannot be lost or misplaced. Furthermore, the appearance of the present invention is attractive and pleasing to the eye. The glasses and pencil can be inserted and removed from the holder without requiring the wearer to remove the hat and the glasses can be placed in the front or back of the hat or cap.

Additionally, many companies pay athletes for the right to place their corporate logo in a prominent position on an athlete's cap. Traditionally, this location has been the front of the cap. This invention allows glasses to be placed in the back of the cap, which does not obscure the logo in the front. The holding mechanism on the sides of the cap also allow for the placement of additional markings or logos on the sides of the cap.

Further objects and advantages will become apparent from a consideration of the ensuing description and drawings.

SUMMARY

It is the object of the present invention to provide an assembly for attachment to or modification of a cap, hat, clothing or other item with a means to securely carry glasses and a pencil while not in use by the wearer. An assembly is provided with a flap secured with a fastener which permits a temple of a pair of glasses and a pencil to be inserted into and securely held in place and an outer side designed to receive identifying or advertising indicia

DETAILED DESCRIPTION OF THE INVENTION

Figure 1:
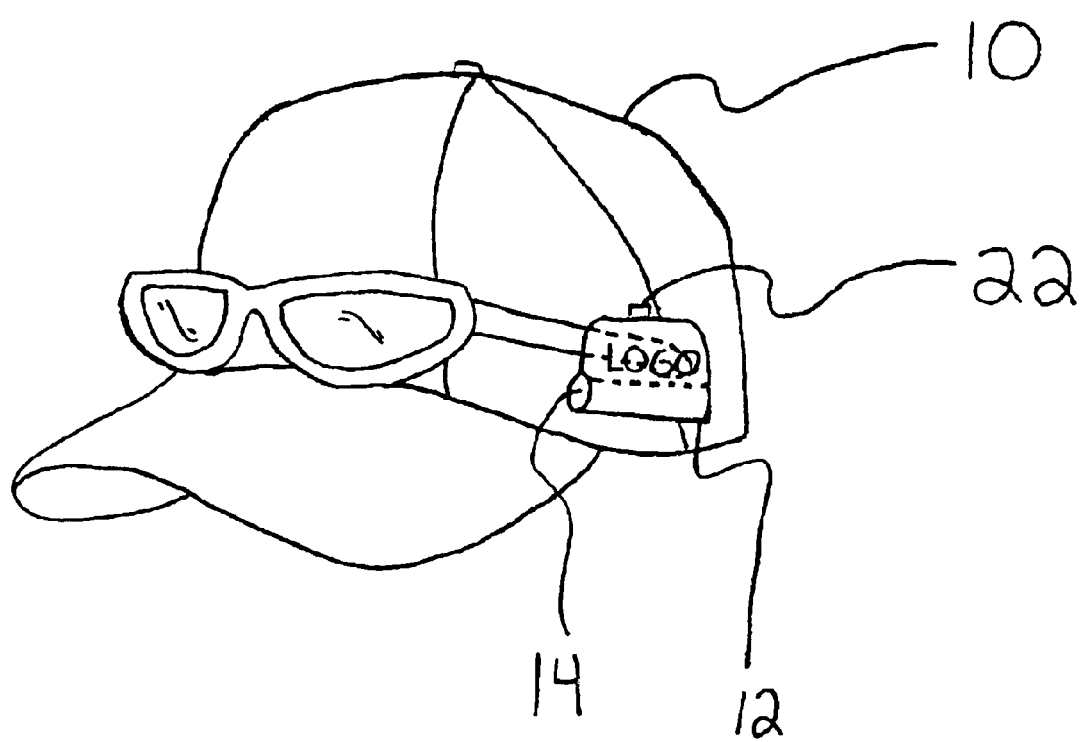
FIG. 1 is a side view of a cap according to the present retaining assembly.

Next, the present invention is explained in detail hereunder, referring to an embodiment thereof shown in the drawings.

Numeral 10 denotes a cap or hat referred to in the claims and other part of the specification. Numeral 12 denotes the eyeglass and pencil retaining assembly attached to the side of the cap 10.

To form the device, a piece of material is folded onto itself to form a loop 14 for the insertion of a pencil or other implement. The material is sewn 20, to securely form the loop 14. A hook-and-loop fastener 16 is attached to the inside flaps on the device. When attached this hook-and-loop fastener will allow the temple of a pair of glasses (sunglasses) to be firmly held in place.

Tab 22 is attached to outside 18 of the retaining assembly to allow for easy opening to insert the temple of a pair of glasses (sunglasses).

The outer side of the eyeglass and pencil retaining assembly 18 can be decorated with a logo or some other type of marking.

Figure 2:
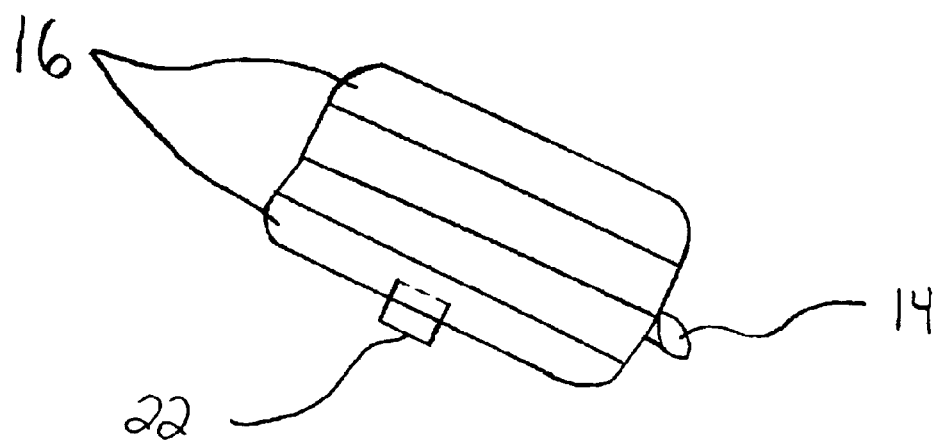
FIG. 2 is a view of the retaining assembly in the open position.
Figure 3:
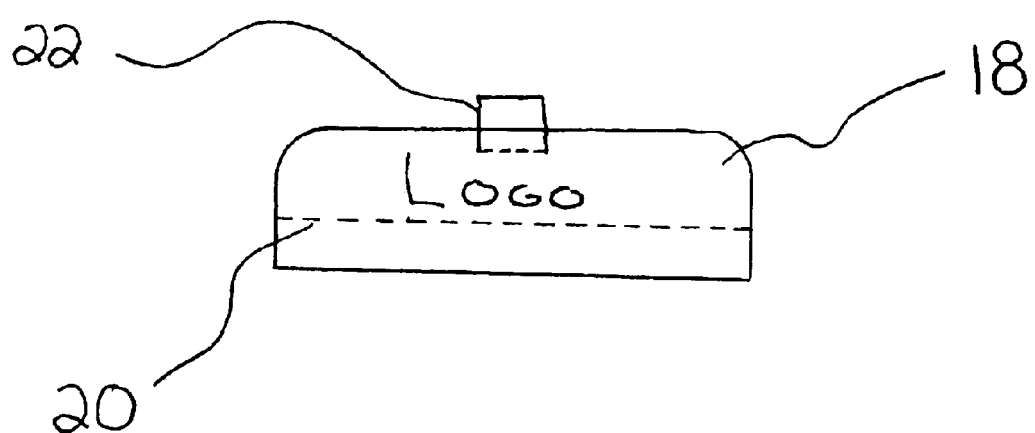
FIG. 3 is a view of the retaining assembly in the closed position.

The device as shown in FIG. 2 and FIG. 3 can be attached by various means to a cap as in FIG. 1, it is understood that the device is also applicable to other articles such as clothing.

What is claimed as being new and desired to be protected by Letters Patent of the United States is as follows:

1. A retaining assembly for retaining eyeglasses, sunglasses or other eyewear and a pencil or other implement to a hat or cap, comprising:
    (a) a means for attaching the retaining assembly to the sides of a hat or cap,
    (b) a flexible material forming a flap and a loop, the temple of a pair of eyeglasses are inserted into the flap and the flap closes securely using a hook and loop fastener to hold the eyeglasses in place on the outside of the cap,
    (c) the loop formed from the flexible material, allows for the insertion of a pencil or other implement for storage,
    (d) a tab attached to the flap to allow the wearer of the cap to open the flap, place the temple of the glasses inside the assembly and securely close the flap, without removing the cap from the wearers head.

2. The assembly of claim 1, where the outer surface of the assembly can include a logo or some other type of marking.

3. The assembly of claim 1, where the wearer can choose to place the glasses in the front of the cap, or the back of the cap.

* * * * *